United States Patent [19]

Takagi et al.

[11] Patent Number: 5,726,340
[45] Date of Patent: Mar. 10, 1998

[54] METHOD OF PRODUCING AROMATIC CARBONATE

[75] Inventors: Masatoshi Takagi; Katsufumi Kujira; Takahiro Yoneyama; Yuji Ohgomori, all of Ibaraki, Japan

[73] Assignee: Mitsubishi Chemical Corporation, Tokyo, Japan

[21] Appl. No.: 796,673

[22] Filed: Mar. 4, 1997

[30] Foreign Application Priority Data

Apr. 5, 1996 [JP] Japan ................... 8-83767

[51] Int. Cl.$^6$ ................... C07C 68/00
[52] U.S. Cl. ................ 558/274; 558/270; 558/271; 558/272; 558/273
[58] Field of Search ................ 558/274, 270, 558/271, 272, 273

[56] References Cited

U.S. PATENT DOCUMENTS 5,498,789 3/1996 Takagi et al. ............ 558/270
5,543,547 8/1996 Hiroshi et al. .

*Primary Examiner*—Michael G. Ambrose
*Attorney, Agent, or Firm*—Oblon, Spivak, McClelland, Maier & Neustadt, P.C.

[57] ABSTRACT

The present invention relates to a method of producing an aromatic carbonate by reacting an aromatic hydroxy compound, carbon monoxide, and oxygen, wherein the reaction is carried out in the presence of a catalyst comprising:

(A) at least one selected from palladium and palladium compounds;
(B) at least one lead compound;
(C) at least one cobalt compound; and,
(D) at least one halide.

According to this method an aromatic carbonate which produces only a small amount of impurities and has excellent selectivity can be produced.

9 Claims, No Drawings

1

METHOD OF PRODUCING AROMATIC CARBONATE

BACKGROUND OF THE INVENTION

1. Field of the Invention

The present invention relates to a method of producing an aromatic carbonate. In particular, it relates to a method of producing an aromatic carbonate which produces only a small amount of impurities and has excellent selectivity. Aromatic carbonates are useful compounds as raw materials for organic synthesis, and diphenyl carbonate is particularly useful as a raw material for polycarbonate and the like.

2. Description of the Related Art

Conventionally, a method of reacting an aromatic hydroxy compound with phosgene has been used for producing aromatic carbonates. However, a switchover for this method is desired because of the high toxicity of phosgene.

Some methods have thus been proposed which do not use phosgene in which an aromatic carbonate is produced from an aromatic hydroxy compound, carbon monoxide and oxygen.

The catalyst used in such methods can be found in the following. Japanese Patent Publication No. 56-38144 discloses a method which uses as a catalyst a palladium compound, a compound containing a metal selected from the group IIIA, IVA, VA, VIA, IB, IIB, VIB or VIIB in the periodic table, and a base. Japanese Patent Publication No.56-38145 discloses a method which uses a palladium compound, a manganese or cobalt complex, a base and a desiccating agent. Japanese Patent Laid-Open No. 1-165551 discloses a method which uses a palladium compound, iodine and zeolite. Japanese Patent Laid-Open No. 2-104564 discloses a method which uses a palladium compound, a divalent or trivalent manganese compound, a tetraalkylammonium halide and a quinone. Japanese Patent Laid-Open No. 2-142754 discloses a method which uses a palladium compound, a divalent or trivalent cobalt compound, a tetraalkylammonium halide and a quinone. Japanese Patent Laid-Open No. 5-25095 discloses a method which uses palladium or a palladium compound, a cobalt compound, a halide and a basic compound. Japanese Patent Laid-Open No. 5-39247 discloses a method which uses a palladium compound, a copper compound, a quinone and onium halide. Japanese Patent Laid-Open No. 5-58961 discloses a method which uses at least one of palladium and a palladium compound, a cobalt compound and an alkali metal halide. Japanese Patent Laid-Open No.5-97775 discloses a method which uses a catalyst comprising palladium, a quaternary ammonium salt, a metallic cocatalyst selected from cobalt, iron, cerium, manganese, molybdenum, samarium, vanadium, chromium and copper, and an organic cocatalyst selected from aromatic ketones, aliphatic ketones and aromatic polycyclic hydrocarbons. Japanese Patent Laid-Open No. 6-9505 discloses a method which uses a palladium compound, a cerium compound, and a quaternary ammonium salt. Japanese Patent Laid-Open No. 6-41020 discloses a method which uses a palladium compound, a metallic cocatalyst selected from manganese, cobalt and copper, and a nitrile compound. Japanese Patent Laid-Open No.6-172268 discloses a method which uses a palladium compound, a cobalt pentacoordinate complex, and a quaternary onium salt. Japanese Patent Laid-Open No.6-172269 discloses a method which uses an inorganic cocatalyst selected from palladium compounds, cobalt, manganese and copper, and an organic cocatalyst such as quaternary onium salts and terpyridine. Japanese Patent Laid-Open No.62-11750 discloses a method which uses a palladium compound, a mono-valent or divalent copper compound, and an ammonium halide compound. Japanese Patent Laid-Open No.7-188116 discloses a method in which a precious metal catalyst is activated with carbon monoxide then used as the catalyst. Japanese Patent Laid-Open No.7-247243 discloses a method in which a reaction is carried out while the resulting water is removed by evaporation.

On the other hand, EP No.0663388 discloses a method which uses a palladium compound, a lead compound, and a quaternary ammonium or quaternary phosphonium halide. According to this method, aromatic carbonates can be produced extremely efficiently, however, when a quaternary ammonium or quaternary phosphonium halide, which is one of the constituents of the catalyst, is reacted with an aromatic hydroxy compound, a large amount of halogenation product of aromatic hydroxy compounds such as bromophenols, are produced as a by-product, resulting in insufficient halides to stop the reaction. In order to solve this problem, a copper compound is added according to the invention described in said specification, however, production of the halogenation products of aromatic hydroxy compounds cannot be completely suppressed thereby.

SUMMARY OF THE INVENTION

It is an object of the present invention to provide a method of efficiently producing an aromatic carbonate by completely suppressing the production of halogenation products of aromatic hydroxy compounds.

As a result of earnest investigation by the inventors for achieving the above-mentioned objective, the inventors found that the use of additional cobalt compound as a catalyst component allows efficient production of desired aromatic carbonates without producing halogenation products of aromatic hydroxy compounds as a by-product to achieve the present invention.

Accordingly, the present invention relates to a method of producing an aromatic carbonate by reacting an aromatic hydroxy compound, carbon monoxide and oxygen, wherein reaction is effected in a reaction system in the presence of catalyst comprising:

(A) at least one selected from palladium and palladium compounds;
(B) at least one lead compound;
(C) at least one cobalt compound; and,
(D) at least one halide.

Therefore, according to the method of the present invention, the production of halogenation products of the aromatic hydroxy compounds can be completely suppressed and the consumption of the catalytic component can be controlled. The method of the present invention is industrially of great value.

DETAILED DESCRIPTION OF THE INVENTION

1. Reaction Raw Material (1) Aromatic Hydroxy Compound

The aromatic hydroxy compounds used in the present invention are an aromatic mono- or poly-hydroxy compounds. Examples of such hydroxy compounds include phenol; substituted phenols such as cresol, xylenol, trimethylphenol, tetramethylphenol, ethylphenol, propylphenol, methoxyphenol, ethoxyphenol, chlorophenol, dichlorophenol, bromophenol, dibromophenol and isomers thereof; naphthol, substituted naphthols such as methylnaphthol, ethylnaphthol, chloronaphthol, bromonaphthol and isomers thereof, various bisphenols such as 2,2-bis(4-hydroxyphenyl)propane; various biphenols; various heteroaromatic hydroxy compounds and isomers thereof; and alkyl or halogen substitution products of the above compounds. Of these compounds, phenol is most preferred.

(2) Carbon Monoxide

The carbon monoxide used in the present invention may be high-purity carbon monoxide or carbon monoxide diluted with another gas such as nitrogen, argon, and carbon dioxide which have no negative effects on the reaction.

(3) Oxygen

The oxygen used in the present invention may be high-purity oxygen, air or oxygen diluted with another gas such as nitrogen, argon, and carbon dioxide, which have no negative effects on the reaction.

2. Catalyst

The catalyst used in the method of the present invention comprises a combination system containing at least one selected from the compounds exemplified in each of components (A)–(D) below, and contains the four components of (A)–(D).

(A) Palladium or Palladium Compound

Examples of palladium or palladium compounds that can be used in the present invention include palladium black; supported palladium such as palladium/carbon, palladium/alumina, palladium/silica and the like; inorganic palladium salts such as palladium chloride, palladium bromide, palladium iodide, palladium sulfate, palladium nitrate and the like; organic palladium salts such as palladium acetate, palladium oxalate and the like. Further, palladium (II) acetylacetonate, a palladium complex compound such as $PdCl_2$ $(PhCN)_2$, $PdCl_2$ $(PPh_3)_2$, $Pd(CO)$ $(PPh_3)_3$, $[Pd(NH_3)_4]Cl_2$, $Pd(C_2H_2)$ $(PPh_3)_2$, $[(\pi^3-C_3H_5)PdCl]_2$, $Pd$ $(DBA)_2$, $Pd_2$ $(DBA)_3CHCl_3$ [Ph indicates phenyl group, DBA indicates dibenzylideneacetone] in which carbon monoxide, nitriles, amines, phosphines or olefins are coordinated around the palladium, or a mixture of palladium and a compound which can produce the above complex compound in the reaction system. Palladium supported on carbon and palladium acetate are particularly preferred.

The molar ratio of the palladium component to the aromatic hydroxy compound is preferably within the range $10^{31\ 7}$ to $10^{-2}$ more preferably $10^{-6}$ to $10^3$.

(B) Lead Compound

The lead compound used in the present invention is preferably soluble in a liquid phase under reaction conditions. Examples of such lead compounds include lead oxides such as $PbO$, $Pb_3O_4$, $PbO_2$ and the like; organic acid salts of lead such as $Pb(OAc)_2$, $Pb(OAc)_4$, $Pb(C_2O_4)$, $Pb(OCOC_2H_5)_2$ and the like; inorganic lead salts such as $Pb(NO_3)_2$, $PbSO_4$ and the like; alkoxy and aryloxy lead such as $Pb(OMe)_2$, $Pb(OPh)_2$ and the like, lead complex compounds such as phthalocyanine lead and the like. Of these compounds, lead oxides and lead compounds represented by the formula $Pb(OR)_2$ (wherein R indicates an aryl group having a carbon number of 6 to 10, or an acyl group having an alkyl group having a carbon number of 1 to 4) are preferred.

Although the amount of the lead compound used in reaction is not limited, the molar ratio to the aromatic hydroxy compound is preferably within the range of $10^{-4}$–$10^{-1}$, more preferably within the range of $10^{-4}$–$10^{-2}$.

(C) Cobalt Compound

A preferable example of the cobalt compound used according to the process of the present invention includes a divalent or trivalent cobalt compound, or a neutral cobalt complex. Other examples include halides ($CoBr_2$ and the like), inorganic acid salts ($Co(NO_3)_2$ and the like), organic acid salts ($Co(OAc)_2$ and the like) and complex compounds ($Co(N,N'$-bis(salicylidene) ethylenediamine) and the like). However, of these compounds, organic acid salts and complexes which are soluble in the reaction system are preferably used. Illustrative examples include $Co$ $(OAc)_2$, $Co(OCOC_2H_5)_2$, $Co(OCOPh)_2$, $Co(pyridine-2-carboxylate)_2$, $Co(acetylacetonate)_2$, $Co(acetylacetonate)_3$, $Co(o$-formylphenoxide$)_2$, $Co(tropolonate)_2$, $Co(N,N'$-bis (salicylidene) ethylenediamine) and the like. A neutral cobalt carbonyl complex ($Co_2(CO)_8$) is also preferably employed.

Although the amount of the cobalt component used in the reaction is not limited, the molar ratio to the aromatic hydroxy compound is preferably within the range of $10^{-4}$–$10^{-1}$, particularly preferably within a range of $10^{-4}$–$10^{-2}$.

(D) Halide

Any halide can be used in the process of the present invention as far as it is a salt of a halogen. Examples include quaternary ammonium halides, quaternary phosphonium halides, alkali metal halides, and alkaline earth metal halides. Preferably used is quaternary ammonium halides which are represented by the following formula:

$R^1R^2R^3R^4NX$ [wherein any of $R^1$–$R^4$ can be the same or different groups selected from $C_1$–$C_{10}$ alkyl or aryl group, X represents a halogen.] Particularly preferable is a bromide, and examples include quaternary ammonium salts such as tetra-n-butylammonium bromide and tetramethylammonium bromide.

Although the amount of the halide used in reaction is not limited, the molar ratio to the aromatic hydroxy compound is preferably within the range of $10^{-4}$–1, more preferably within the range of $10^{-3}$–$10^{-1}$.

3. Reaction Conditions

Reaction is effected in a reactor in which a catalyst consisting of the components (A), (B), (C) and (D) are charged under pressure of carbon monoxide and oxygen and heated with sufficient stirring.

In the reaction, the absolute total pressure is within the range of 1 to 500 atm, preferably 1 to 250 atm. The composition ratio between carbon monoxide and oxygen is preferably beyond the explosive range of these gases in view of safety. The partial pressures of carbon monoxide and oxygen are preferably 30 to 100 atm and 1 to 10 atm, respectively.

The reaction temperature is within the range of 20° to 300° C., preferably 80° to 250° C.

Although the reaction time depends upon reaction conditions, the reaction time is generally several minutes to several hours.

In reaction, an organic additive including an aromatic diol such as hydroquinone, an oxidation product thereof such as quinone, or amine, all of which are used in conventional catalyst systems, may be added to the reaction system.

An inert solvent such as hexane, heptane, cyclohexane, benzene, toluene, xylene, methylene chloride, chloroform, chlorobenzene, diethyl ether, diphenyl ether, tetrahydrofuran, dioxane, acetonitrile or nitrobenzene can be used.

EXAMPLES

The present invention will be described in detail below with reference to the examples and comparative examples.

The reaction results were obtained by gas chromatography analysis using n-pentadecane as an internal standard (Capillary column BPX-5 (available from SGE Co., Ltd) ;50° C.→300° C.).

EXAMPLE 1

3.01 g (32 mmol) of phenol, 25.54 mg (12 μmol Pd) of 5% palladium/carbon (available from N.E.Chemcat Co., Ltd), 2.68 mg (12 μmol) of lead (II) oxide, 2.99 mg (12 μmol) of cobalt (II) acetate tetrahydrate, and 77.3 mg (0.24 mmol) of tetrabutylammonium bromide were charged in a 40-ml Hastelloy autoclave. After the air in the system was replaced by carbon monoxide, 60 atm of carbon monoxide and 30 atm of dry air were introduced into the autoclave, followed by stirring at 100° C. for 3 hours by induction stirring. After reaction, the liquid phase was quantitatively analyzed by gas chromatography. As a result, diphenyl carbonate was obtained with a yield of 5.64% (0.90 mmol) based on phenol. Bromophenols were not observed.

COMPARATIVE EXAMPLE 1

The same reaction as that in Example 1 was carried out except that cobalt (II) acetate tetrahydrate was not used. As a result, diphenyl carbonate was obtained with a yield of 8.38% (1.33 mmol) based on phenol. Bromophenols (o- and p-bromophenols were observed, but m-bromophenol was not observed, and the same applies hereinafter.) were produced as by-products in an amount of 54.0% (0.127 mmol) based on the tetrabutylammonium bromide used.

EXAMPLES 2 TO 4

The same reaction as that in Example 1 was effected except that 2.55 mg (1.2 μmol) of 5% palladium/carbon was used, 37.0 mg (0.24 mmol) of tetramethylammonium bromide was used in place of tetrabutylammonium bromide, and 12 μmol each of various cobalt compounds was used in place of cobalt (II) acetate tetrahydrate. The formula of the cobalt compounds used, the yield and the amount of resulting diphenyl carbonate, and the amount and the production rate of the resulting bromophenols based on the tetramethylammonium bromide used, are shown in Table 1.

COMPARATIVE EXAMPLE 2

The same reaction as that in Example 2 was carried out except that a cobalt compound was not used. The yield and the amount of resulting diphenyl carbonate and the amount and the production rate of the resulting bromophenols based on tetramethylammonium bromide used are shown in Table 1.

COMPARATIVE EXAMPLE 3

The same reaction as that in Example 3 was carried out except that lead (II) oxide was not used. The yield of diphenyl carbonate was 0.93% (0.15 mmol).

COMPARATIVE EXAMPLE 4

The same reaction as that in Example 4 was carried out except that lead (II) oxide was not used. The yield of diphenyl carbonate was 0.80% (0.13 mmol).

TABLE 1

| Example No. | 2 | 3 | 4 | 5 |
|---|---|---|---|---|
| Co compound | $Co_2(CO)_3$ | $Co(pic)_2$ | $Co(trop)_2$ | none |
| DPC (%/PhOH) | 4.23 | 3.51 | 4.12 | 9.14 |
| DPC (mmol) | 0.68 | 0.57 | 0.66 | 1.46 |
| BR (%/Br$^-$) | ND | ND | ND | 9 |
| BP (mmol) | ND | ND | ND | 0.127 |

DPC: diphenyl carbonate
BP: bromophenols
pic: pyridine-2-carboxylate
trop: tropolonate
ND: not detected

What is claimed is:

1. A method of producing an aromatic carbonate by reacting an aromatic hydroxy compound, carbon monoxide and oxygen, wherein the reaction is carried out in the presence of a catalyst comprising;

(A) at least one selected from palladium and palladium compounds:

(B) at least one lead compound:

(C) at least one cobalt compound: and (D) at least one halide.

2. A method according to claim 1, wherein the component (A) is palladium acetate or palladium supported on carbon.

3. A method according to claim 1, wherein the component (B) is a lead oxide or a lead compound represented by the formula $Pb(OR)_2$ wherein R is an aryl group having a carbon number of 6 to 10, or an acyl group having an alkyl group with a carbon number of 1 to 4.

4. A method according to claim 1, wherein the component (C) is a neutral cobalt complex, or a divalent or trivalent cobalt compound having an organic residue.

5. A method according to claim 1, wherein the component (D) is a bromide.

6. A method according to claim 5, wherein the component (D) is a quaternary ammonium salt of a bromide.

7. A method according to claim 1, wherein the aromatic hydroxy compound is phenol.

8. A method according to claim 1, wherein the molar ratio of the component (A) to the aromatic hydroxy compound is within the range of $10^{-7}$ to $10^{-2}$, that of the component (B) to the aromatic hydroxy compound is within $10^{-4}$ to $10^{-1}$, that of the compound (C) to the aromatic hydroxy compound is within $10^{-4}$ to $10^{-1}$ and that of the compound (D) to the aromatic hydroxy compound is within $10^{-4}$ to 1.

9. A method according to claim 1, wherein the aromatic carbonate is diphenyl carbonate.

* * * * *